United States Patent
Nickel et al.

(10) Patent No.: US 6,693,119 B2
(45) Date of Patent: *Feb. 17, 2004

(54) INDOLYL-3-GLYOXYLIC ACID DERIVATIVES HAVING THERAPEUTICALLY VALUABLE PROPERTIES

(75) Inventors: Bernd Nickel, Mühltal (DE); Gerald Bacher, Heidelberg (DE); Thomas Klenner, Ingelheim (DE); Thomas Beckers, Frankfurt (DE); Peter Emig, Bruchköbel (DE); Jürgen Engel, Alzenau (DE); Erik Bruyneel, Harelbeke (BE); Günter Kamp, Münster (DE); Kirsten Peters, Münster (DE)

(73) Assignee: Baxter Healthcare SA, Wallisellen (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/492,531

(22) Filed: Jan. 27, 2000

(65) Prior Publication Data

US 2003/0114511 A1 Jun. 19, 2003

(30) Foreign Application Priority Data

Apr. 2, 1998 (DE) .......................... 19814838
Sep. 28, 1999 (DE) .......................... 19946301

(51) Int. Cl.$^7$ ................................ A61K 31/44
(52) U.S. Cl. ...................................... 514/339
(58) Field of Search ......................... 514/339

(56) References Cited

U.S. PATENT DOCUMENTS

| | | | |
|---|---|---|---|
| 6,008,231 A | * 12/1999 | Lebaut et al. | ................ 514/339 |
| 6,225,329 B1 | 5/2001 | Richter et al. | |
| 6,232,327 B1 | 5/2001 | Nickel et al. | |
| 6,251,923 B1 | 6/2001 | Hofgen et al. | |
| 6,262,044 B1 | 7/2001 | Moller et al. | |

FOREIGN PATENT DOCUMENTS

| | | |
|---|---|---|
| DE | 196 36 150 A1 | 2/1998 |
| WO | WO 99/46237 | 9/1999 |
| WO | WO 99/51224 | 10/1999 |
| WO | WO 99/55696 | 11/1999 |
| WO | WO 00/67802 | 11/2000 |

* cited by examiner

*Primary Examiner*—Jerome D. Goldberg
(74) *Attorney, Agent, or Firm*—Pillsbury Winthrop LLP

(57) ABSTRACT

The invention relates to the use of N-substituted indole-3-glyoxylamides of the general Formula I

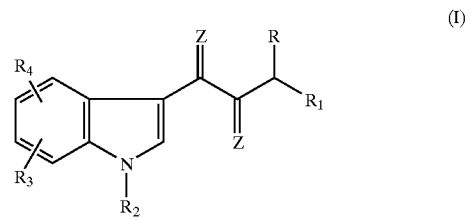

and to pharmaceutical compositions having antitumor action.

12 Claims, 11 Drawing Sheets

Cytotoxic action of D-24851 against MDR murine leukemic subline L1210/VCR

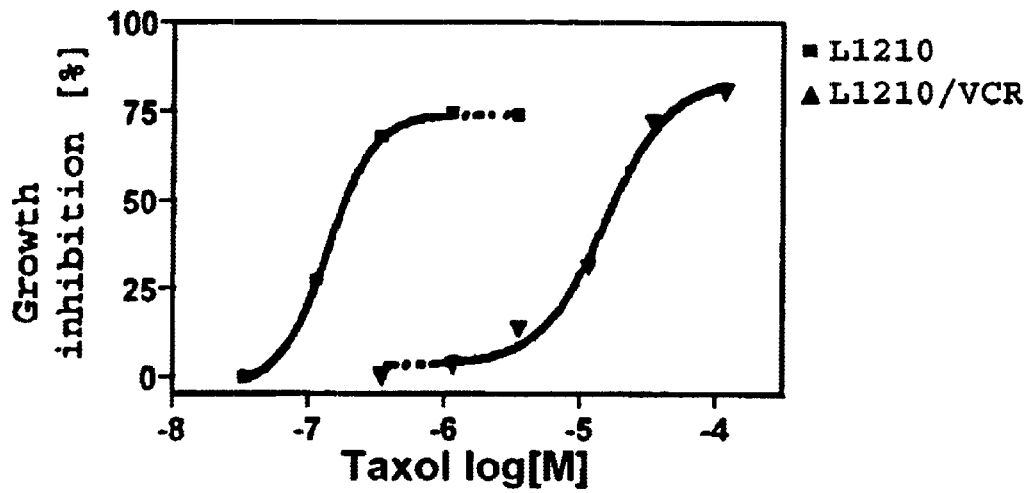

In contrast to Taxol, Doxorubicin, Vincristine or Epothilone B, D-24851 has the same cytotoxic activity against the MDR mouse leukemic subline L1210/VCR as against the normal L1210

*FIG. 1A*

Cytotoxic action of D-24851 against MDR murine leukemic subline L1210/VCR

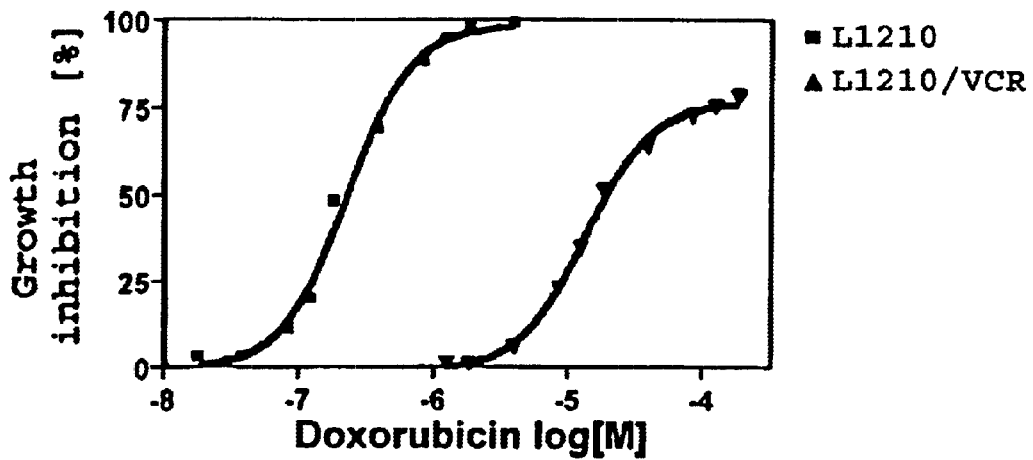

In contrast to Taxol, Doxorubicin, Vincristine or Epothilone B, D-24851 has the same cytotoxic activity against the MDR mouse leukemic subline L1210/VCR as against the normal L1210

*FIG 1B*

In contrast to Taxol, Doxorubicin, Vincristine or Epothilone B, D-24851 has the same cytotoxic activity against the MDR mouse leukemic subline L1210/VCR as against the normal L1210

In contrast to Taxol, Doxorubicin, Vincristine or Epothilone B, D-24851 has the same cytotoxic activity against the MDR mouse leukemic subline L1210/VCR as against the normal L1210

Influence of D-24851 on the multidrug-resistant murine leukemia L1210 (dose 10% of the $LD_{50}$)

| | Dose (mg/kg) | L1210 ILS % | L1210/VCR ILS % |
|---|---|---|---|
| D-24851 | 4 x 100 p.o. | 46 | 42 |
| | 4 x 147 p.o. | 94 | 85 |
| Adriamycin | 4 x 1 i.p. | 158 | 6 |
| Taxol | 4 x 15 i.p. | 82 | 6 |
| Vincristine | 4 x 0.2 i.p. | 47 | -11 |

*FIG. 3*

Incubation of the migration of MO4 cells by D-24851

- □ 0nM D-24851
- ◇ 20nM
- ○ 40nM
- △ 100nM
- ⊟ 260nM
- ◇ 1000nM

• D-24851 inhibits the migration of MO4 cells in a dose-dependent manner
From this, an antiinvasive and an antimetastatic action can be derived for D-24851.

Neurotoxicity

| | D-24851 10x 20 mg/kg p.o | Vincristine 10x 0.2 mg/kg i.p. | Taxol 10x 15 mg/kg i.p. |
|---|---|---|---|
| Ataxia (rat) | -- | + | ++ |
| Traction (rat) | -- | + | ++ |
| Reaction (rat) | -- | ++ | +++ |

+ $p \geq 0.05$ vs. control  ++ $p \geq 0.01$ vs. control  -- = no effect

D-24851 shows no neurotoxicity [sic] in maximally antitumor-active doses in contrast to Taxol and vincristine

*FIG. 6*

Angiogenesis in human endothelial cell culture
Vital staining, 44 hours after induction of angiogenesis DMSO control 0.1 µM D24851

Angiogenesis in human endothelial cell culture
Lethal staining, 22 hours after induction of angiogenesis DMSO control 0.1 µM D24851

INDOLYL-3-GLYOXYLIC ACID DERIVATIVES HAVING THERAPEUTICALLY VALUABLE PROPERTIES

CROSS REFERENCE TO RELATED APPLICATIONS

This claims priority to German Patent Application Nos. 198 14 838.0, filed on Apr. 2, 1998 and 199 46 301.8, filed on Sep. 28, 1999, the contents of both applications are incorporated in their entirely by reference.

BACKGROUND OF THE INVENTION

FIELD OF THE INVENTION

The invention relates to the further advantageous embodiment of the German Patent Application indole-3-glyoxylamides having the reference 19814 838.0.

BACKGROUND INFORMATION

In connection with chemotherapy in the case of oncoses, the greatest problems result due to the occurrence of pharmaceutical resistance on the one hand and due to the serious side effects of these agents on the other hand.

In addition, it is known that after reaching a certain size many primary tumors prematurely tend to metastasis formation via the blood stream and lymphatic tracts. The progressive process of tumor invasion and the formation of metastases is the most frequent cause of death of the cancer patients.

There are various approaches for explaining this spread, inter alia enhanced angiogenesis, increased extracellular matrix degradation, tumor cell migration and modulation of cell adhesion. These factors can also interact but to date are only partially resolved.

The metastatic spread of a tumor is usually accompanied by poor prognoses in tumor treatment. The prerequisite for metastatic spread is the detachment of cells from the primary tumor, the migration of cells to the blood vessels, invasion into the blood vessels and invasion of the cells from the blood vessels into other tissue.

An inhibitory action of certain oncostatic agents such as tamoxoifen on the migration and invasion of cancer cells is known [J Clin Endocrinol Metab 1995 January; 80(1): 308–13].

The inhibition of tumor cell invasion by verapamil has been reported [Pigment Cell Res 1991 December; 4(5–6): 225–33.]

The influence of melantonin on invasive and metastatic properties of MCF-7 human breast cancer cells has been reported [Cancer res Oct. 1, 1998; 58(19): 4383–90].

In the published PCT Application WO 96/23506, the overcoming of pharmaceutical resistance in certain tumor pharmaceuticals was demonstrated as a result of the gene amplification of the multi-drug resistance gene (MDR gene) brought about by such oncostatic agents.

Oncostatic agents such as vincristine and Taxol furthermore have a not inconsiderable neurotoxicity, which proves disadvantageous in chemotherapy.

The object of the invention is then to widen the field of use of N-substituted indole-3-glyoxylamides and thus to enrich the available pharmaceutical wealth. The possibility of a lower, longer-lasting and better-tolerable medication for the class of substances having antitumor action described in German Patent Application 19814 838.0 should thus be opened up. In particular, the disadvantageous development of resistance, as is known of many antitumor agents, should be circumvented.

Moreover, development and spread of the tumor due to metastases should be counteracted.

According to more recent knowledge, as angiogenesis is obviously responsible for tumor growth and the development of metastases, the property of angiogenesis inhibition represents a further advantageous pharmaceutical potential, for example, in cancer therapy.

The increase in action achieved with the N-substituted indole-3-glyoxylamides should more effectively shape pharmaceutical consumption in tumor therapy. Moreover, it should be possible to shorten the period of treatment and to extend it in therapy-resistant cases. In addition, relapses and metastases should be restricted or prevented and thus the survival period of the patients additionally increased. The aim is to develop medicaments which can intervene in the process of metastatic spread.

It has surprisingly been found that the N-substituted indole-3-gloxylamides described in German Patent Application 19814 838.0, of the general formula 1 described below, which are suitable for the treatment of oncoses, further have those advantageous properties for tumor treatment which can extend their area of use.

SUMMARY OF THE INVENTION

The invention relates to the use of N-substituted indole-3-gloxylamides according to claim 1 general formula 1a for tumor treatment in particular in the case of pharmaceutical resistance and metastasizing carcinoma and for the suppression of metastasis formation, and also as angiogenesis inhibitors,

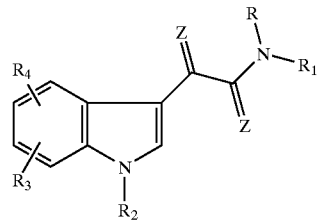

Formula 1 where the radicals R, $R_1$, $R_2$, $R_3$, $R_4$ and Z have the following meaning:

R=hydrogen, $(C_1-C_6)$-alkyl, where the alkyl group can be mono- or polysubstituted by the phenyl ring and this phenyl ring for its part can be mono- or polysubstituted by halogen, $(C_1-C_6)$-alkyl, $(C_3-C_7)$-cycloalkyl, by carboxyl groups, carboxyl groups esterified with $C_1-C_6$-alkanols, trifluoromethyl groups, hydroxyl groups, methoxy groups, ethoxy groups, benzyloxy groups and by a benzyl group which is mono- or polysubstituted in the phenyl moiety by $(C_1-C_6)$-alkyl groups, halogen atoms or trifluoromethyl groups, R is further the benzyloxycarbonyl group (z group) and the tertiary-butoxycarbonyl radical (BOC radical), furthermore the acetyl group.

$R_1$ can be the phenyl ring, which is mono- or polysubstituted by $(C_1-C_6)$-alkyl, $(C_1-C_6)$-alkoxy, cyano, halogen, trifluoromethyl, hydroxyl, benzyloxy, nitro, amino, $(C_1-C_6)$-alkylamino, $(C_1-C_6)$-alkoxycarbonylamino and by the carboxyl group or by the carboxyl group esterified with $C_1-C_6$-alkanols, or can be a pyridine structure of the formula 2 and its N-oxide

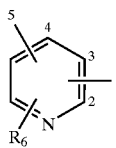

Formula 2 and its N-oxide, where the pyridine structure is alternatively bonded to the ring carbon atoms 2, 3 and 4 and can be substituted by the substituents $R_5$ and $R_6$. The radicals $R_5$ and $R_6$ can be identical or different and have the meaning $(C_1-C_6)$-alkyl and the meaning $(C_3-C_7)$-cycloalkyl, $(C_1-C_6)$-alkoxy, nitro, amino, hydroxyl, halogen and trifluoromethyl and further are the ethoxycarbonylamino radical and the group carboxyalkyloxy in which the alkyl group can have 1–4 C atoms.

$R_1$ can further be a 2- or 4-pyrimidinyl heterocycle, where the 2-pyrimidinyl ring can be mono- or polysubstituted by the methyl group, furthermore are the 2-, 3-, and 4- and 8-quinolyl structure substituted by $(C_1-C_6)$-alkyl, halogen, the nitro group, the amino group and the $(C_1-C_6)$-alkylamino radical, are a 2-, 3- and 4-quinolylmethyl group, where the ring carbons of the pyridylmethyl radical of the quinolyl group and of the quinolylmethyl radical can be substituted by $(C_1-C_6)$-alkyl, $(C_1-C_6)$-alkoxy, nitro, amino and $(C_1-C_6)$-alkoxycarbonylamino.

$R_1$, in the case in which R=hydrogen, the methyl or benzyl group and the benzyloxycarbonyl radical (Z radical), the tert-butoxycarbonyl radical (BOC radical) and the acetyl group, can furthermore be the following radicals: —CH$_2$COOH; —CH(CH$_3$)—COOH; —(CH$_3$)$_2$—CH—(CH$_2$)$_2$—CH—COO; H$_3$C—H$_2$C—CH(CH$_3$)—CH(COOH)—; HO—H$_2$C—CH(COOH)—; phenyl-CH$_2$—CH(COOH)—; (4-imidazolyl)-CH$_2$—CH—(COOH)—; HN=C(NH$_2$)—NH—(CH$_2$)$_3$—CH(COOH)—; H$_2$N—(CH$_2$)$_4$—CH(COOH)—; H$_2$N—CO—CH$_2$—CH—(COOH)—; HOOC—(CH$_2$)$_2$—CH(COOH)—;

$R_1$, in the case in which R is hydrogen, the Z group, the BOC radical, the acetyle or the benzyl group, can furthermore be the acid radical of a natural or unnatural amino acid, e.g., the α-glycyl, the α-sarcosyl, the α-alanyl, the α-leucyl, the α-isoleucyl, the α-seryl, the α-phenylalanyl, the α-histidyl, the α-prolyl, the α-arginyl, the α-lysyl, the α-asparagyl and the α-glutamyl radical, where the amino groups of the respective amino acids can be present unprotected or can be protected. A possible protective group of the amino function is the carbobenzoxy radical (Z radical) and the tert-butoxycarbonyl radical (BOC radical) as well as the acetyl group. In the case of the asparagyl and glutamyl radical claimed for $R_1$, the second, unbonded carboxyl group is present as a free carboxyl group or in the form of an ester with $C_1-C_6$-alkanols, e.g., as a methyl, ethyl or as a tert-butyl ester.

Furthermore, $R_1$ can be the allylaminocarbonyl-2-methylprop-1-yl group. R and $R_1$ can further form, together with the nitrogen atom to which they are bonded, a piperazine ring of the formula III or a homopiperazine ring, provided $R_1$ is an aminoalkylene group, in which

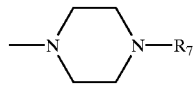

Formula 3

$R_7$ is an alkyl radical, is a phenyl ring which can be mono- or polysubstituted by $(C_1-C_6)$-alkyl, $(C_1-C_6)$-alkoxy, halogen, the nitro group, the amino function and by the $(C_1-C_6)$-alkylamino group. $R_7$ is furthermore the benzhydryl group and the bis-p-fluorobenzylhydryl group.

$R_2$ can be hydrogen and the $(C_1-C_6)$-alkyl group, where the alkyl group is mono- or polysubstituted by halogen and phenyl, which for its part can be mono- or polysubstituted by halogen, $(C_1-C_6)$-alkyl, $(C_3-C_7)$-cycloalkyl, carboxyl groups, carboxyl groups esterified with $C_1-C_6$-alkanols, trifluoromethyl groups, hydroxyl groups, methoxy groups, ethoxy groups or benzyloxy groups. The $(C_1-C_6)$-alkyl group counting as $R_2$ can further be substituted by the 2-quinolyl group and the 2-, 3- and 4-pyridyl structure, which can both in each case be mono- or polysubstituted by halogen, $(C_1-C_4)$-alkyl groups or $(C_1-C_4)$-alkoxy groups. $R_2$ is further the aroyl radical, where the aryl moiety on which this radical is based is the phenyl ring, which can be mono- or polysubstituted by halogen, $(C_1-C_6)$-alkyl, $(C_3-C_7)$-cycloalkyl, carboxyl groups, carboxyl groups esterified with $C_1-C_6$-alkanols, trifluoromethyl groups, hydroxyl groups, methoxy groups, ethoxy groups or benzyloxy groups.

$R_3$ and $R_4$ can be identical or different and are hydrogen, $(C_1-C_6)$-alkyl, $(C_3-C_7)$-cycloalkyl, $(C_1-C_6)$-alkanoyl, $(C_1-C_6)$-alkoxy, halogen and benzyloxy. $R_3$ and $R_4$ can furthermore be the nitro group, the amino group, the $(C_1-C_4)$-mono or dialkyl-substituted amino group, and the $(C_1-C_6)$-alkoxycarbonylamino function or $(C_1-C_6)$-alkoxycarbonylamino-$(C_1-C_6)$-alkyl function.

Z is O and S.

The designation alkyl, alkanol, alkoxy or alkylamino group for the radicals R, $R_1$, $R_2$, $R_3$, $R_4$, $R_5$, $R_6$, $R_7$ is normally understood as meaning both "straight-chain" and "branched" alkyl groups, where "straight-chain alkyl groups can be, for example, radicals such as methyl, ethyl, n-propyl, n-butyl, n-pentyl, n-hexyl and "branched alkyl groups" designate, for example, radicals such as isopropyl or tert-butyl. "Cycloalkyl" is understood as meaning radicals such as, for example, cyclopropyl, cyclobutyl, cyclopentyl, cyclohexyl or cycloheptyl.

The designation "halogen" represents fluorine, chlorine, bromine or iodine. The designation "alkoxy group" represents radicals such as, for example, methoxy, ethoxy, propoxy, butoxy, isopropoxy, isobutoxy or pentoxy.

The compounds can also be employed as acid addition salts, for example as salts of mineral acids, such as, for example, hydrochloric acid, sulfuric acid, phosphoric acid, salts of organic acids, such as, for example, acetic acid, lactic acid, malonic acid, maleic acid, fumaric acid, gluconic acid, glucuronic acid, citric acid, embonic acid, methanesulfonic acid, trifluoroacetic acid, succinic acid and 2-hydroxyethanesulfonic acid.

Both the compounds of the formula 1 and their salts are biologically active.

The compounds of the formula 1 can be administered in free form or as salts with physiologically tolerable acids.

Administration can be performed orally, parenterally, intravenously, transdermally or by inhalation.

The invention furthermore relates to pharmaceutical preparations which contain at least one of the compounds of the formula 1 or their salts with physiologically tolerable inorganic or organic acids and, if appropriate, pharmaceutically utilizable excipients and/or diluents or auxiliaries.

Suitable administration forms are, for example, tablets, coated tablets, capsules, solutions for infusion or ampoules, suppositories, patches, powder preparations which can be employed by inhalation, suspensions, creams and ointments.

The preparation processes for the substances can be taken from the examples of German Patent DE 196 36 150 A1.

The therapeutically valuable properties found relate specifically to the following advantages:
- no development of resistance was detected
- parameters were detected which are characteristic of the inhibition of metastasis formation (migration)
- parameters were found which confirm the inhibition of neovascularization (angiogenesis)
- in various models, it was not possible to find any neurotoxicity with the N-substituted indole-3-gloxylamides according to claim 1 general formula 1a in contrast to most antitumor preparations.

The development of resistance which is not present is confirmed in the following pharmacological models and cell cultures:
1. The cytotoxic activity of N-(pyridin-4-yl)-[1-(4-chlorobenzyl)-indole-3-yl]glyoxylamide (see claim 4) on the MDR (multidrug-resistant) leukemia cell line of the mouse L 1210/VCR is not influenced in vivo and in vitro. See FIGS. 1, 2 and 3.

N-(pyridin-4-yl)-[1-(4-chlorobenzyl)-indole-3-yl] glyoxylamide (see claim 4) has an unchanged cytotoxic activity against the multidrug-resistant mouse leukemia cell subline L1210/VCR in contrast to Taxol, doxirubicin, vincristine or epotholone B.

BRIEF DESCRIPTION OF THE DRAWINGS

FIG. 3 shows the influence on the multi-drug-resistant murine leukemia L1210 (dose 10% of the $LD_{50}$).

FIG. 6 shows a comparison of neurotoxicity induced by compound D-24851 versus other neoplastic agents.

DETAILED DESCRIPTION OF THE INVENTION

Experimental Procedure

The mouse leukemia cell lines L 120 was adapted to vincristine. The unadapted (L 1210) and the adapted (L 1210/VCR) cells were exposed to cytostatic agents and the cell growth, which was determined by the metabolic activity, was determined (XTT test). The curves which connect the XTT data points were calculated using a nonlinear regression program. These experimental results were also confirmed in vitro on the human resistant LT 12/MDR cell line. See FIG. 4.

Figure 1C:
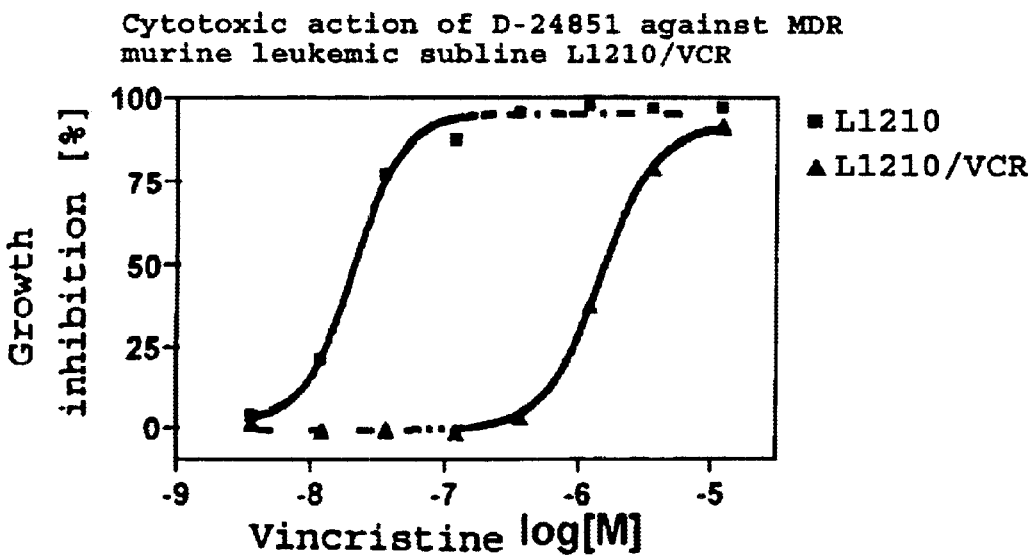
FIG. 1 shows the cytotoxic action of compound D-24851 against MDR murine leukemic subline L1210/VCR.
Figure 1D:
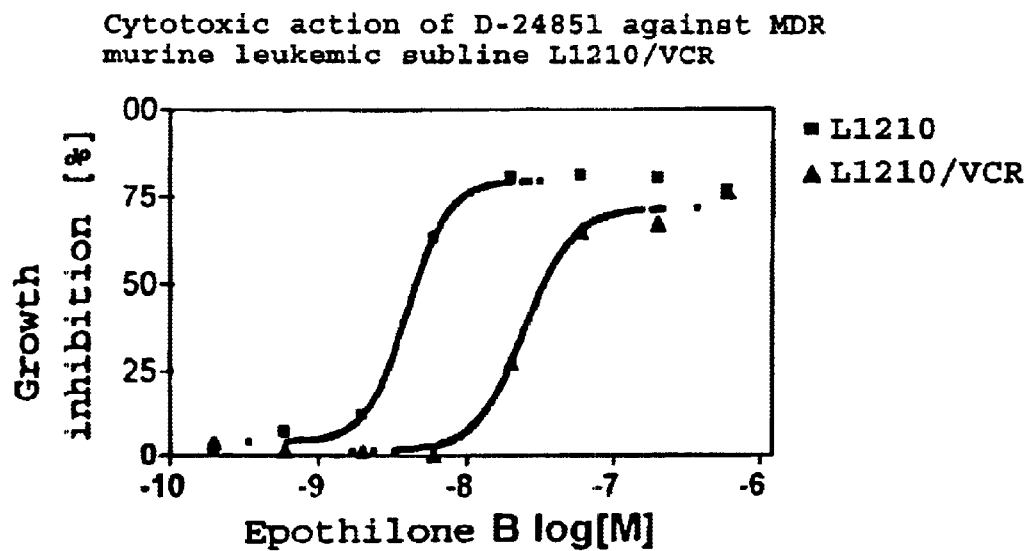
Figure 1E:
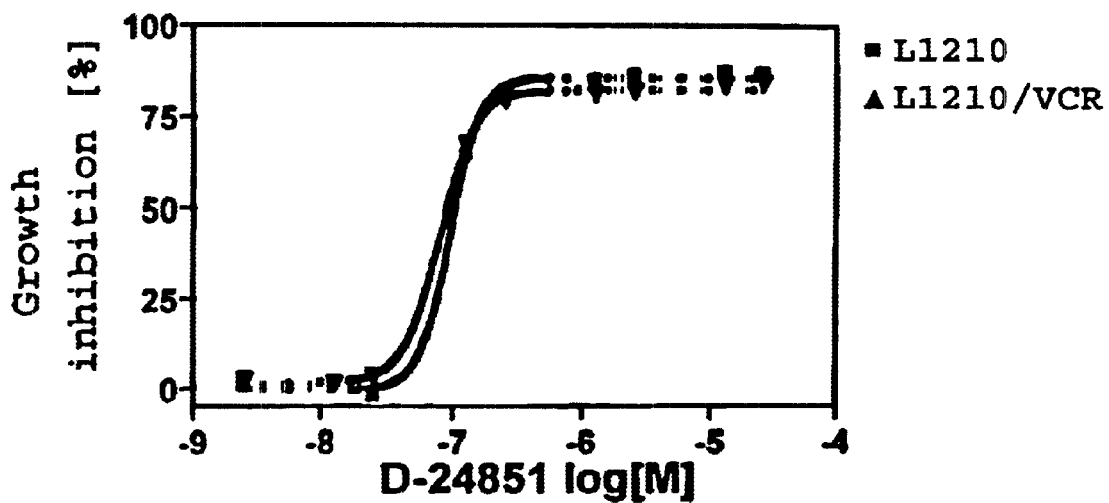
Figure 2:
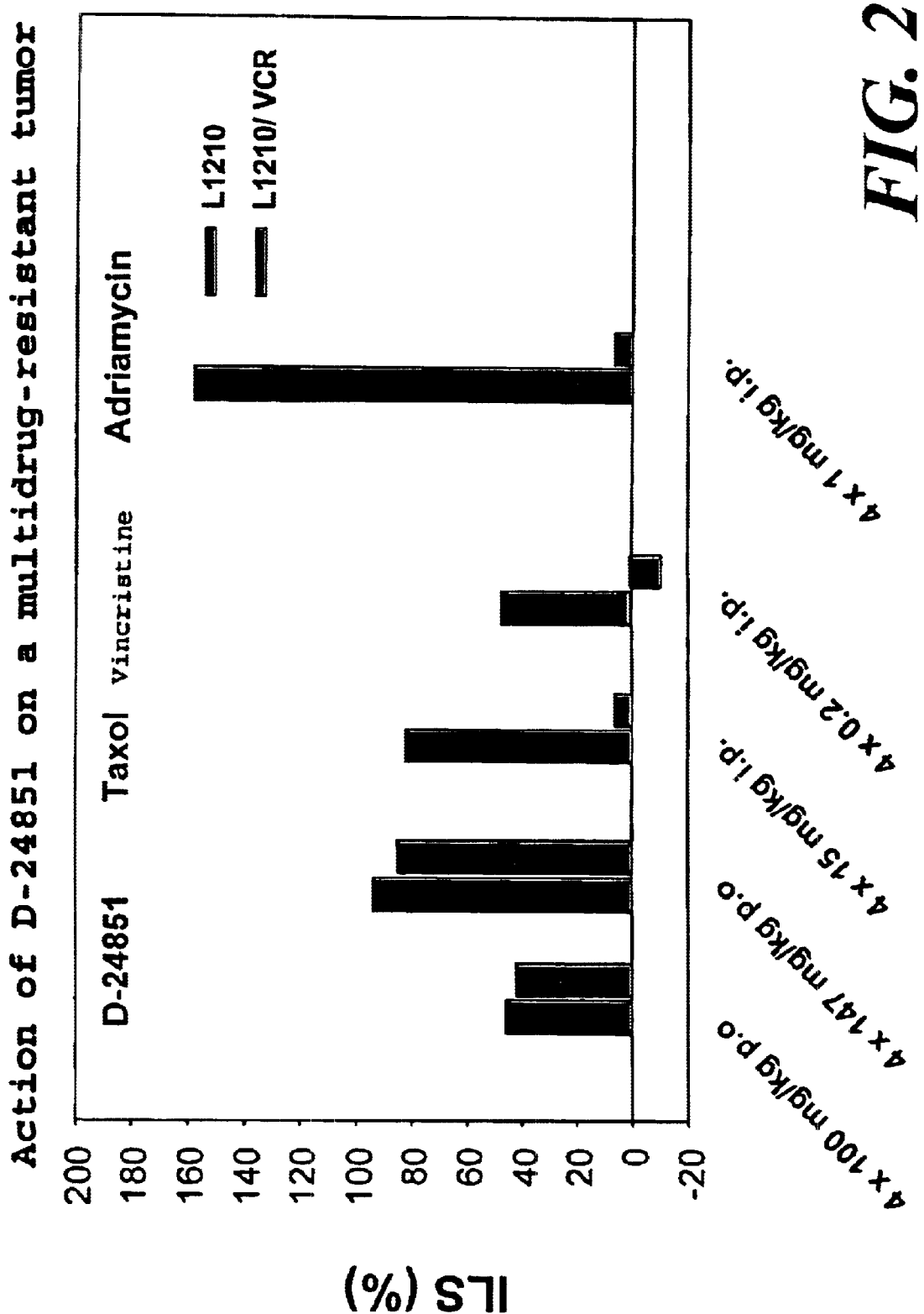
FIG. 2 demonstrates the action of compound D-24851 on a multidrug-resistant tumor.
Figure 4A:
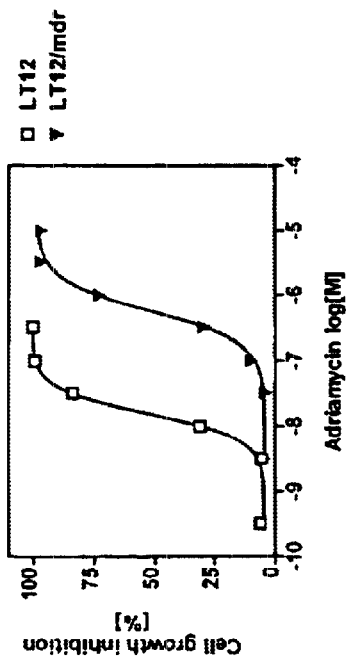
FIG. 4 compares the effect compound D-24851 on human leukemia cells with the effect of other neoplastic agents on the same leukemia cells.
Figure 4B:
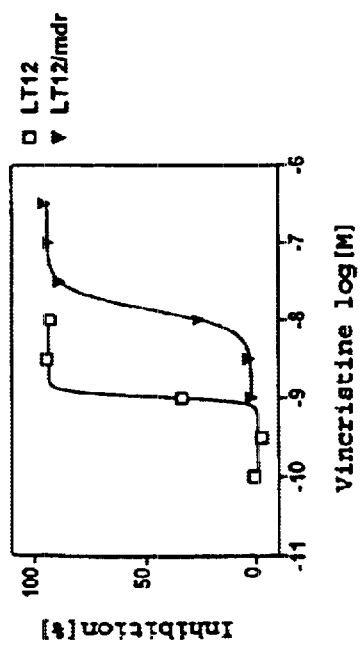
Figure 4C:
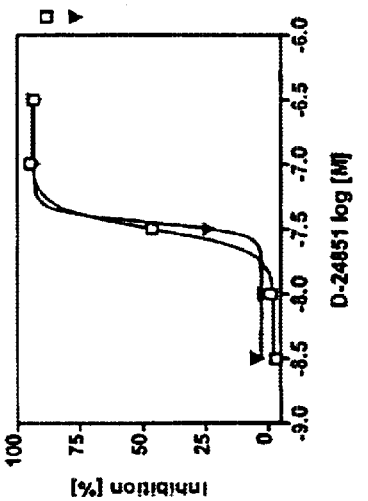
Figure 4D:
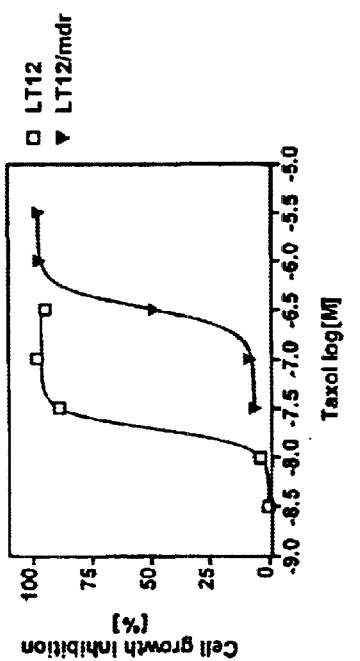
Figure 5:
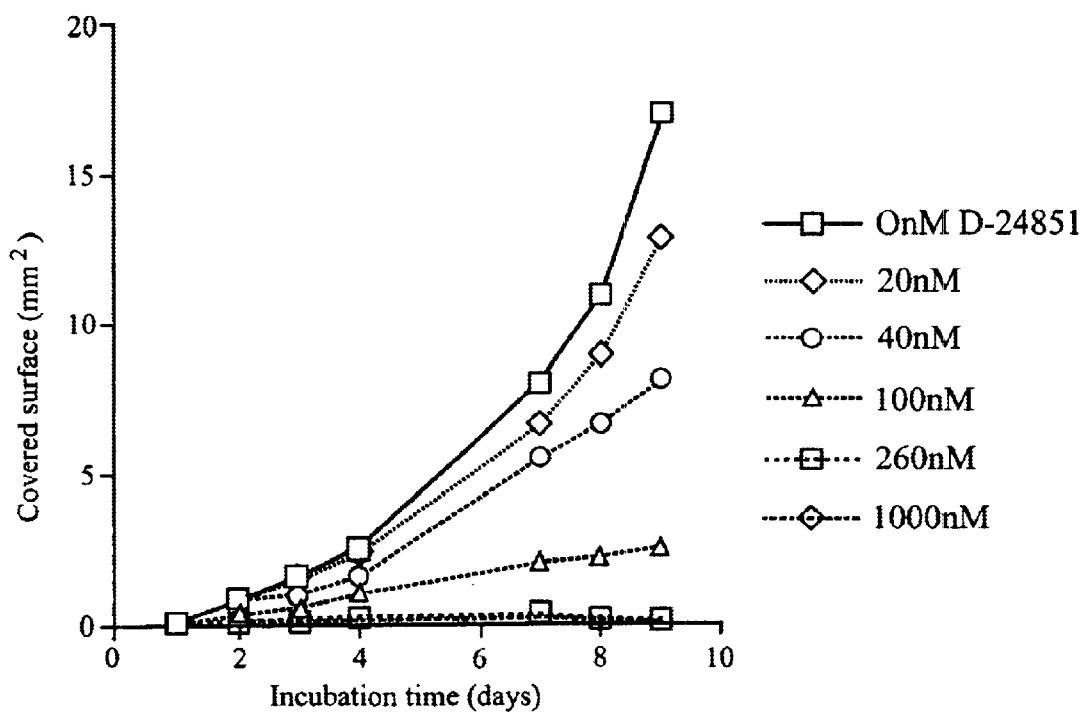
FIG. 5 shows the inhibition of migration of M)4 cells by compound D-24851.

2. The detection of lacking metastasis formation was afforded by means of inhibition of migration of MO4 cells. See FIG. 5.

N-(pyridin-4-yl)-[1-(4-chlorobenzyl)-indole-3-yl] glyoxylamide (see claim 4) inhibits the migration of MO4 cells in a dose-dependent manner. From this, an antiinvasive and an antimetastatic action can be derived for N-(pyridin-4-yl)-[1-(4-chlorobenzyl)-indole-3-yl]glyoxylamide.

The migration ability of MO4 cells can be measured in vitro by inoculating cells into the center of a cell culture dish and determining the migration by means of radius or the covered area of the cells after various days with and without N-(pyridin-4-yl)-[1-(4-chlorobenzyl)-indole-3-yl] glyoxylamide. FIG. 4 shows that the migration of the cells decreases with increasing N-(pyridin-4-yl)-[1-(4-chlorobenzyl)-indole-3-yl]glyoxylamide concentration.

In order to test whether N-(pyridin-4-yl)-[1-(4-chlorobenzyl)-indole-3-yl]glyoxylamide also acts antiinvasively, the invasion of MO4 fibrosarcoma cells into chickens' hearts was investigated. It is also seen here that at a concentration of 260 and 1000 nM the invasion is completely inhibited, whereas at lower concentrations the invasiveness of the MO4 cells increases. On the basis of these findings, it is seen that N-(pyridin-4-yl)-[1-(4-chlorobenzyl)-indole-3-yl]glyoxylamide inhibits both the migration and the invasion of tumor cells and thereby has a strong antimetastatic potential.

3. From comparison experiments of the compound according to the invention N-(pyridin-4-yl)-[1-(4-chlorobenzyl)-indole-3-yl]glyoxylamide (see claim 4) with vincristine and Taxol on rats, where ataxia, traction and reaction were assessed (see FIG. 6), it is evident that this compound shows no neurotoxic effect, in contrast to Taxol and vincristine.

Figure 7:
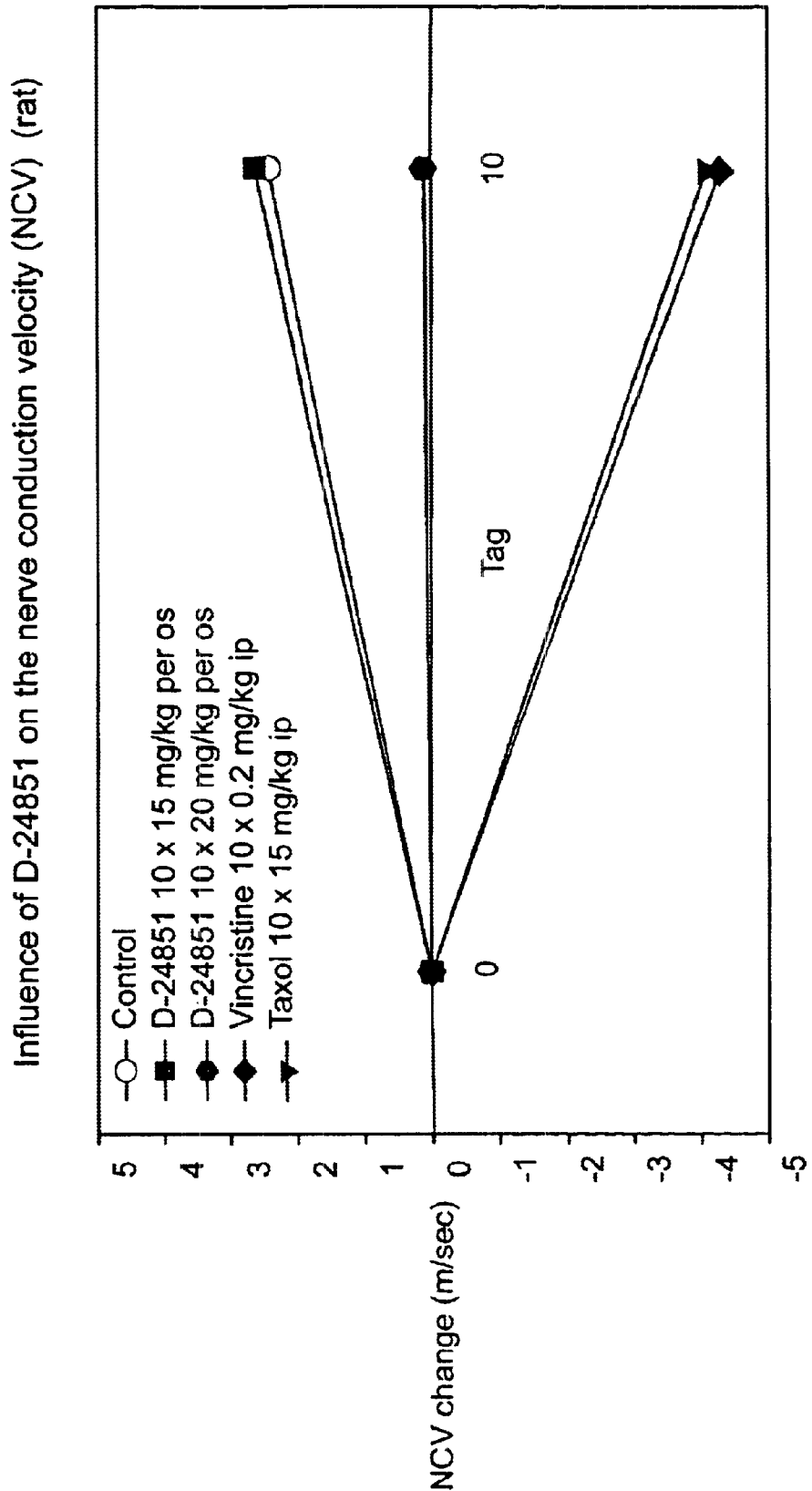
FIG. 7 shows the influence of compound D-24851 on nerve conduction velocity in rat.

Furthermore, in comparison to Taxol and vincristine, N-(pyridin-4-yl)-[1-(4-chlorobenzyl)-indole-3-yl] glyoxylamide has no negative influence on the nerve conduction velocity. See FIG. 7.

This confirms that N-(pyridin-4-yl)-[1-(4-chlorobenzyl)-indole-3-yl]glyoxylamide, on account of the absent neurotoxicity, has clearly lower side effects than other chemotherapeutics.

Figure 8:
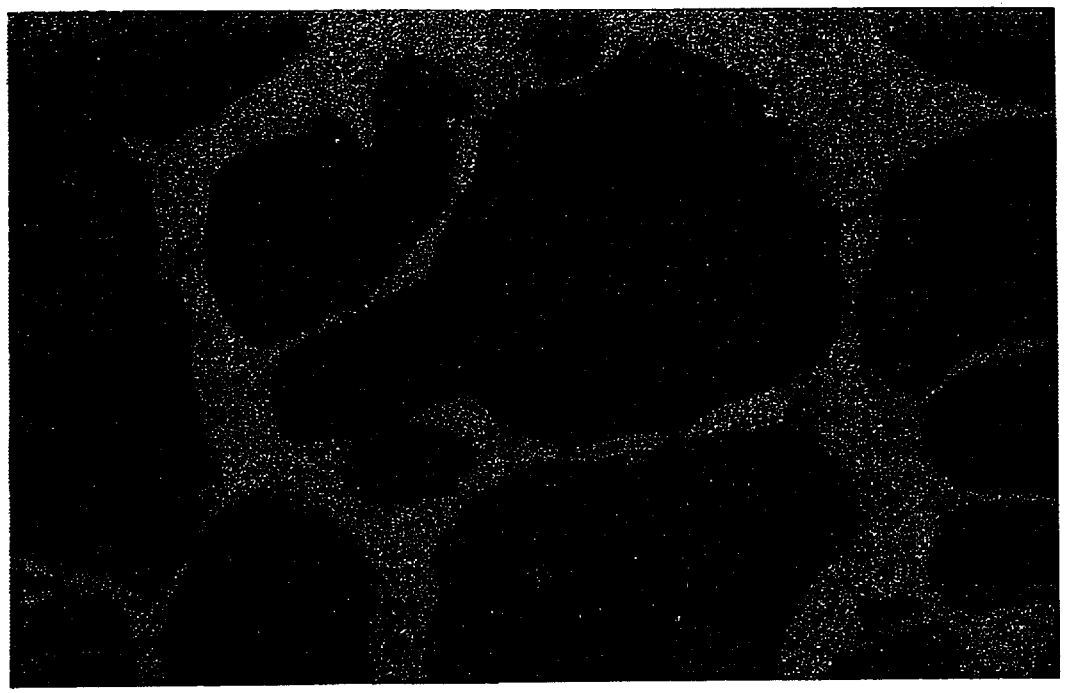
FIG. 8 compares angiogenesis in human endothelial cells in compound D-24851-treated cells versus DMSO (44 hours after induction of angiogenesis).
Figure 8:
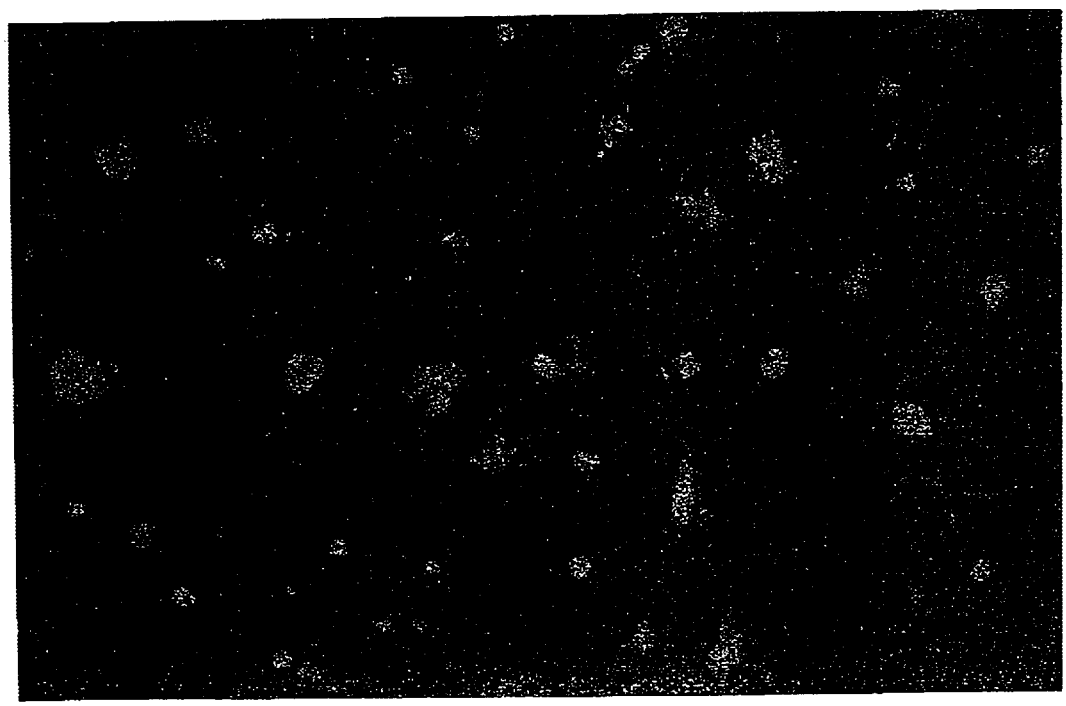
Figure 9:
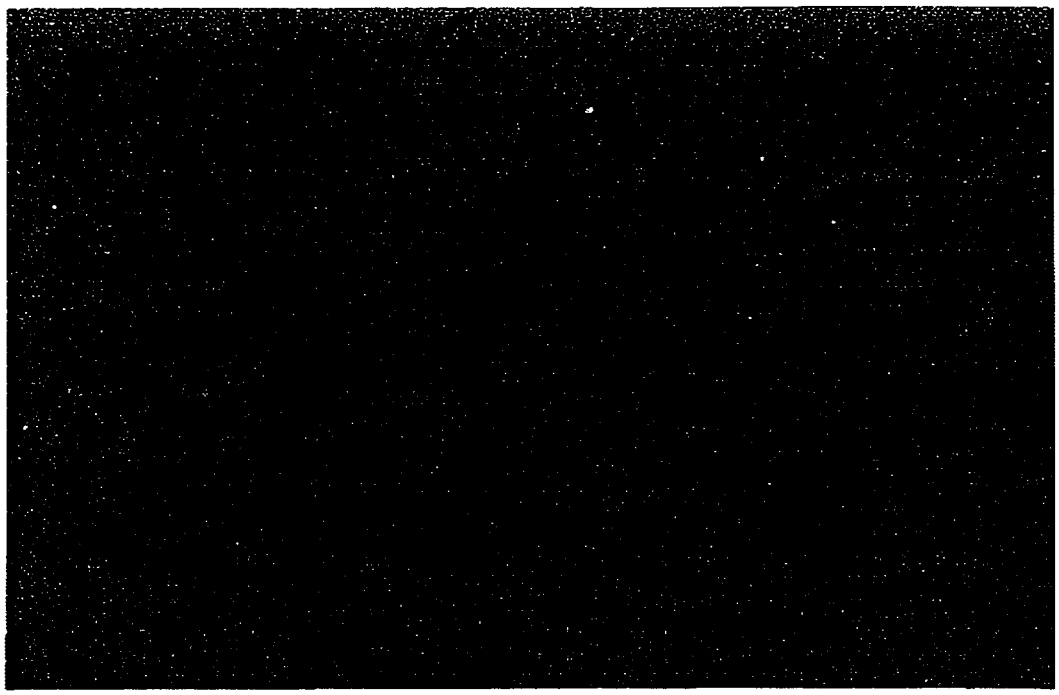
FIG. 9 compares angiogenesis in human endothelial cells in compound D-24851-treated cells versus DMSO (22 hours after induction of angiogenesis).
Figure 9:

4. From further investigations as shown in FIGS. 8 and 9, it is evident that the compound N-(pyridin-4-yl)-[1-(4-chlorobenzyl)-indole-3-yl]glyoxylamide (see claim 4) has a potential as an angiogenesis inhibitor. As a result of the physiological relationship with tumor growth, angiogenesis inhibitors are simultaneously also agents for the inhibition of tumor growth, in that the formation of new blood vessels, which are intended to feed the tumor, is inhibited.

In vitro in an antiangiogenesis model on endothelial cells, N-(pyridin-4-yl)-[1-(4-chlorobenzyl)-indole-3-yl] glyoxylamide causes a complete inhibition of vascularization, which is not based on a cytotoxic effect.

It can be seen in FIG. 8 that N-(pyridin-4-yl)-[1-(4-chlorobenzyl)-indole-3-yl]glyoxylamide almost completely breaks up existing cell-cell contacts due to 0.1 μMol/l of N-(pyridin-4-yl)-[1-(4-chlorobenzyl)-indole-3-yl] glyoxylamide (see vital staining). Normally, the cells maintain at least partial contact. Cell migration is markedly reduced, many cells are rounded. Lethal staining in a monolayer before angiogenesis induction did not show any increased cell mortality with N-(pyridin-4-yl)-[1-(4-chlorobenzyl)-indole-3-yl]glyoxylamide. Even in the first 22 hours after induction, no increased cell mortality was yet discernible in comparison with the control. (See lethal staining in FIG. 9, white points)

The cells originated from human umbilical vein (arterial function). They were employed for the investigation in the third and fourth passage. Angiogenesis is triggered by a natural stimulus. The primary trigger of endothelial migration is a protein which is expressed to an increased extent in vascularizing tissue. The substances are added to the culture medium shortly before induction of angiogenesis.

The concentration for the antiangiogenetic action of N-(pyridin-4-yl)-[1-(4-chlorobenzyl)-indole-3-yl] glyoxylamide is markedly below the concentration for the cytotoxic activity. As a result, it is possible to separate the two action qualities (cytotoxic activity and antiangiogenetic action) from one another.

Without wanting to restrict the scope of the invention by the following statements, it can be said that doses from about 20 mg up to 500 mg daily are possible orally.

On intravenous administration as an injection or as an infusion, up to 250 mg/day or more can be administered depending on the body weight of the patient and individual tolerability.

As a result of the lacking development of resistance and suppression of metastasis, a high effectiveness and wide use of the agents for even in tumor-refractory patients can be expected.

The antiangiogenesis effect is suitable for additionally suppressing the spread of the tumor. However, the invention also comprises the use of the N-substituted indole-3-gloxylamides according to claim 1 general formula 1a in further disorders in which an angiogenesis inhibitory effect is functionally desired (e.g., would healing).

In addition, the invention also relates to the fixed or free combination of the N-substituted indole-3-gloxylamides according to claim 1 general formula 1a with antitumor agents known per se, and also the replacement of antitumor agents which have become ineffective as a result of resistance development by N-substituted indole-3-gloxylamides according to claim 1 general formula 1a.

What is claimed is:

1. A method of treating antitumor agent resistant tumors, metastasizing carcinoma including development and spread of metastases, tumors sensitive to angiogenesis inhibitors or tumors that are both antitumor agent resistant and sensitive to angiogenesis inhibitors, comprising administration to a patient suffering from an antitumor agent resistant tumor, a metastasizing carcinoma including development and spread of metastases, a tumor sensitive to angiogenesis inhibitors or a tumor that is both antitumor agent resistant and sensitive to angiogenesis inhibitors of an effective amount of one or more N-substituted indole-3-glyoxylamides of formula I

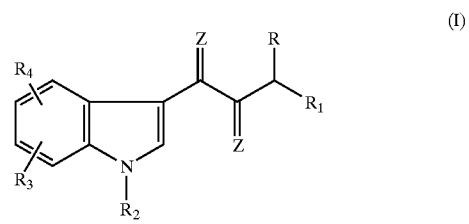

wherein each of R, $R_1$, $R_2$, $R_3$, $R_4$ and Z have the following meanings:

R is hydrogen, a benzyloxycarbonyl group, a tertiary-butoxycarbonyl radical, an acetyl group or a $(C_1-C_6)$-alkyl, wherein the alkyl group is monosubstituted or polysubstituted by a phenyl ring, the phenyl ring is monosubstituted or polysubstituted by a member selected from the group consisting of halogens, $(C_1-C_6)$-alkyl groups, $(C_3-C_7)$-cycloalkyl groups, carboxyl groups, carboxyl groups esterified with $(C_1-C_6)$-alkanols, trifluoromethyl groups, hydroxyl groups, methoxy groups, ethoxy groups, benzyloxy groups and a benzyl group which is monosubstituted or polysubstituted with a member selected from the group consisting of $(C_1-C_6)$-alkyl groups, halogen atoms and trifluoromethyl groups;

$R_1$ is a phenyl ring, which is monosubstituted or polysubstituted with a member of the group consisting of $(C_1-C_6)$-alkyl, $(C_1-C_6)$-alkoxy, cyano, halogen, trifluoromethyl, hydroxyl, benzyloxy, nitro, amino, $(C_1-C_6)$-alkylamino, $(C_1-C_6)$-alkoxycarbonylamino, carboxyl group, carboxyl group esterified with $(C_1-C_6)$-alkanols, and pyridine moiety of formula 2 or an N-oxide of a pyridine moiety of formula 2;

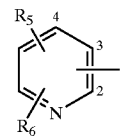

wherein the pyridine moiety is alternatively bonded to ring carbon atoms 2, 3 and 4 and can be substituted by substituents $R_5$ and $R_6$, and wherein radicals $R_5$ and $R_6$ can be identical or different and may be $(C_1-C_6)$-alkyl, $(C_3-C_7)$-cycloalkyl, $(C_1-C_6)$-alkoxy, nitro, amino, hydroxyl, halogen, trifluoromethyl, an ethoxycarbonylamino radical or a carboxyalkyloxy group in which the alkyl group can have 1–4 C atoms; or $R_1$ is a 2-pyrimidinyl heterocycle or 4-pyrimidinyl heterocycle, having a 2-pyrimidinyl ring that is monosubstituted or polysubstituted with a methyl group, a 2-, 3-, 4- or 8-quinolyl structure substituted by $(C_1-C_6)$-alkyl, halogen, a nitro group, an amino group or a $(C_1-C_6)$-alkylamino radical, or a 2-, 3- or 4-quinolylmethyl group, wherein ring carbons of the pyridylmethyl radical of the quinolyl group and of the quinolylmethyl radical can be substituted by $(C_1-C_6)$-alkyl, $(C_1-C_6)$-alkoxy, nitro, amino or $(C_1-C_6)$-alkoxycarbonylamino;

wherein when R is hydrogen, a methyl benzyl group, a benzyloxycarbonyl radical, a tert-butoxycarbonyl radical or an acetyl group, $R_1$, may be the following radicals: —$CH_2COOH$; —$CH(CH_3)$=$COOH$; —$(CH_3)_2$—$CH$—$(CH_2)_2$—$CH$—$COO$—; $H_3C$—$H_2C$—$CH(CH_3)$—$CH(COOH)$—; $HO$—$H_2C$—$CH(COOH)$—; phenyl-$CH_2$—$CH(COOH)$—; (4-imidazolyl)-$CH_2$—$CH$—$(COOH)$—; $HN$=$C(NH_2)$—$NH$—$(CH_2)_3$—$CH(COOH)$—; $H_2N$—$(CH_2)_4$—$CH(COOH)$—; $H_2N$—$CO$—$CH_2$—$CH$—$(COOH)$—; $HOOC$—$(CH_2)_2$—$CH(COOH)$—;

wherein when R is hydrogen, the Z radical, the tertiary-butoxycarbonyl radical, an acetyl group or a benzyl group, $R_1$, is an acid radical of a natural amino acid or unnatural amino acid selected from the group consisting of α-glycyl, α-sarcosyl, α-alanyl, α-leucyl, α-isoleucyl, α-seryl, α-phenylalanyl, α-histidyl, α-prolyl, α-arginyl, α-lysyl, α-asparagyl and α-glutamyl radical, wherein an amino group of the amino acid is unprotected or protected by a member of the group consisting of a carbobenzoxyl radical, a tert-butoxycarbonyl radical and an acetyl group, wherein when $R_1$ is an asparagyl or glutamyl radical, a second, unbonded carboxyl group is present as a free carboxyl group or in the form of an ester with $(C_1-C_6)$-alkanol as a methyl, ethyl or as a tert-butyl ester, or $R_1$ is an allylamino-carbonyl-2-methylprop-1-yl group;
wherein
R and $R_1$ optionally form, together with the nitrogen atom to which they are bonded, a piperazine ring of formula 3 or a homopiperazine ring, provided $R_1$ is an aminoalkylene group, in which

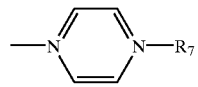

(III)

$R_7$ is an alkyl radical, a phenyl ring which can be monosubstituted or polysubstituted by a $(C_1-C_6)$-alkyl, a $(C_1-C_6)$-alkoxy, a halogen, a nitro group, an amino functions, or a $(C_1-C_6)$-alkylamino group, or $R_7$ is a benzhydryl group or a bis-p-fluorobenzylhydryl group;

$R_2$ is hydrogen or a $(C_1-C_6)$-alkyl group, wherein the alkyl group is monosubstituted or polysubstituted by halogen and phenyl group that is monosubstituted or polysubstituted by halogen, $(C_1-C_6)$-alkyl, $(C_3-C_7)$-cycloalkyl, carboxyl groups, carboxyl groups esterified with $(C_1-C_6)$-alkanols, trifluoromethyl groups, hydroxyl groups, methoxy groups, ethoxy groups or benzyloxy groups, wherein when $R_2$ is a $(C_1-C_6)$-alkyl group, the $(C_1-C_6)$-alkyl group is substituted by a 2-quinolyl group and a 2-, 3- and -pyridyl structure, each of which may be monosubstituted or polysubstituted by one or more halogens, $(C_1-C_6)$-alkyl groups or $(C_1-C_4)$-alkoxy groups, wherein $R_2$ may be an aroyl radical having an aryl moiety comprising a phenyl ring, that is monosubstituted or -polysubstituted by one or more of halogens, $(C_1-C_6)$-alkyls, $(C_3-C_7)$-cycloalkyls, carboxyl groups, carboxy groups esterified with $(C_1-C_6)$-alkanols, trifluoromethyl groups, hydroxyl groups, methoxy groups, ethoxy groups or benzyloxy groups;

$R_3$ and $R_4$ are identical or different and are selected from the group consisting of hydrogen, $(C_1-C_6)$-alkyl, $(C_3-C_7)$-cycloalkyl, $(C_1-C_6)$-alkanoyl, $(C_1-C_6)$-alkoxy, halogen and benzyloxy, a nitro group, an amino group, a $(C_1-C_4)$-mono or dialkyl-substituted amino group, a $(C_1-C_6)$-alkoxycarbonylamino function and a $(C_1-C_6)$-alkoxycarbonylamino-$(C_1-C_6)$-alkyl function; and Z is O or S.

2. A method of treating antitumor agent resistant tumors, metastasizing carcinoma including development and spread of metastases, tumors sensitive to angiogenesis inhibitors or tumors that are both antitumor agent resistant and sensitive to angiogenesis inhibitors, comprising administration to a patient suffering from an antitumor agent resistant tumor, a metastasizing carcinoma including development and spread of metastases, a tumor sensitive to angiogenesis inhibitors or a tumor that is both antitumor agent resistant and sensitive to angiogenesis inhibitors of an effective amount of one or more N-substituted indole-3-glyoxylamides of formula 1a

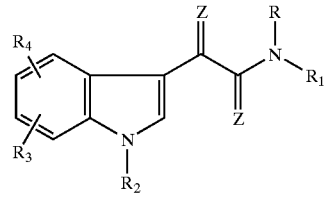

(Ia)

wherein
R is hydrogen;
$R_1$ is 4-pyridyl or 4-fluorophenyl;
$R_2$ is benzyl, 4-chlorobenzyl, 4-fluorobenzyl, 3-pyridylmethyl, or 4-bromobenzyl;
$R_3$ and $R_4$ are hydrogen; and
Z is O,
whereby said method causes fewer neurotoxic side effects to the patient than previously known treatments.

3. The method according to claim 1 or claim 2, wherein the N-substituted indole-3-glyoxylamides are in the form of an acid addition salt of mineral acids and organic acids or an N-oxide thereof,
wherein the mineral acid or organic acid is selected from the group consisting of hydrochloric acid, sulfuric acid, phosphoric acid, acetic acid, lactic acid, malonic acid, maleic acid, fumaric acid, gluconic acid, glucuronic acid, citric acid, embonic acid, methanesulfonic acid, trifluroacetic acid, succinic acid and 2-hydroxyethanesulfonic acid.

4. The method according to claim 1 or claim 2, wherein the N-substituted indole-3-glyoxylamides are in the form of an acid addition salt of mineral acids and organic acids or an N-oxide thereof, wherein the mineral acid or organic acid is selected from the group consisting of hydrochloric acid, sulfuric acid, phosphoric acid, acetic acid, lactic acid, malonic acid, maleic acid, fumaric acid, gluconic acid, glucuronic acid, citric acid, embonic acid, methanesulfonic acid, trifluroacetic acid, succinic acid and 2-hydroxyethanesulfonic acid, and are administered together with a pharmaceutically utilizable excipient, diluent or auxiliary in the form of a tablet, coated tablet, capsule, solution for infusion or ampoule, suppository, patch, or a powder preparation which can be administered by inhalation, suspension, creme or ointment.

5. A method of treating metastasizing carcinoma including development and spread of metastases, comprising administration to a patient suffering from a metastasizing carcinoma including development and spread of metastases of an effective amount of one or more N-substituted indole-3-glyoxylamides selected from the group consisting of:
- N-(pyridin-4-yl)-[1-(4-fluorobenzyl)-indole-3-yl] glyoxylamide,
- N-(pyridin-4-yl)-(1-benzylindole-3-yl)-glyoxylamide,
- N-(4-fluorophenyl)-[1-(3-pyridylmethyl)-indole-3-yl] glyoxylamide,
- N-(pyridin-4-yl)-[1-(4-chlorobenzyl)-indole-3-yl] glyoxylamide and
- N-(pyridin-4-yl)-[1-(4-fluorobenzyl)-indole 3-yl] glyoxylamide HCl, or a physiologically tolerable acid addition salt or N-oxide thereof.

6. A method of treating antitumor agent resistant tumors, tumors sensitive to angiogenesis inhibitors or tumors that are both antitumor agent resistant and sensitive to angiogenesis inhibitors, comprising administration to a patient suffering from an antitumor agent resistant tumor of an effective amount of one or more N-substituted indole-3-glyoxylamides selected from the group consisting of:
- N-(pyridin-4-yl)-[1-(4-fluorobenzyl)-indole-3-yl] glyoxylamide,
- N-(pyridin-4-yl)-(1-benzylindole-3-yl)-glyoxylamide,
- N-(4-fluorophenyl)-[1-(3-pyridylmethyl)-indole-3-yl] glyoxylamide,
- N-(pyridin-4-yl)-[1-(4-chlorobenzyl)-indole-3-yl] glyoxylamide, and
- N-(pyridin-4-yl)-[1-(4-fluorobenzyl)-indole 3-yl] glyoxylamide HCl, or a physiologically tolerable acid addition salt or N-oxide thereof.

7. A method of treating antitumor agent resistant tumors, metastasizing carcinoma including development and spread of metastases, tumors sensitive to angiogenesis inhibitors or tumors that are both antitumor agent resistant and sensitive to angiogenesis inhibitors, comprising administration to a patient suffering from an antitumor agent resistant tumor, a metastasizing carcinoma including development and spread of metastases, a tumor sensitive to angiogenesis inhibitors or a tumor that is both antitumor agent resistant and sensitive to angiogenesis inhibitors of an effective amount of:
- N-(pyridin-4-yl)-[1-(4-fluorobenzyl)-indole-3-yl] glyoxylamide or
- N-(pyridin-4-yl)-[1-(4-fluorobenzyl)-indole-3-yl] glyoxylamide hydrochloride.

8. A method of treating antitumor agent resistant tumors, metastasizing carcinoma including development and spread of metastases, tumors sensitive to angiogenesis inhibitors or tumors that are both antitumor agent resistant and sensitive to angiogenesis inhibitors, comprising administration to a patient suffering from an antitumor agent resistant tumor, a metastasizing carcinoma including development and spread of metastases, a tumor sensitive to angiogenesis inhibitors or a tumor that is both antitumor agent resistant and sensitive to angiogenesis inhibitors of an effective amount of N-(pyridin-4-yl)-(1-benzylindole-3-yl) glyoxylamide or its hydrochloride salt.

9. A method of treating antitumor agent resistant tumors, metastasizing carcinoma including development and spread of metastases, tumors sensitive to angiogenesis inhibitors or tumors that are both antitumor agent resistant and sensitive to angiogenesis inhibitors, comprising administration to a patient suffering from an antitumor agent resistant tumor, a metastasizing carcinoma including development and spread of metastases, a tumor sensitive to angiogenesis inhibitors or a tumor that is both antitumor agent resistant and sensitive to angiogenesis inhibitors of an effective amount of N-(4-fluorophenyl)-[1-(3-pyridylmethyl)-indole-3-yl] glyoxylamide or its hydrochloride salt.

10. A method of treating antitumor agent resistant tumors, metastasizing carcinoma including development and spread of metastases, tumors sensitive to angiogenesis inhibitors or tumors that are both antitumor agent resistant and sensitive to angiogenesis inhibitors, comprising administration to a patient suffering from an antitumor agent resistant tumor, a metastasizing carcinoma including development and spread of metastases, a tumor sensitive to angiogenesis inhibitors or a tumor that is both antitumor agent resistant and sensitive to angiogenesis inhibitors of an effective amount of N-(pyridin-4-yl)-[1-(4-chlorobenzyl)-indole-3-yl] glyoxylamide or its hydrochloride salt.

11. A method of treating antitumor agent resistant tumors, metastasizing carcinoma including development and spread of metastases, tumors sensitive to angiogenesis inhibitors or tumors that are both antitumor agent resistant and sensitive to angiogenesis inhibitors, comprising administration to a patient suffering from an antitumor agent resistant tumor, a metastasizing carcinoma including development and spread of metastases, a tumor sensitive to angiogenesis inhibitors or a tumor that is both antitumor agent resistant and sensitive to angiogenesis inhibitors of an effective amount of (N-(pyridin-4-yl)-[1-(4-fluorobenzyl)-indole-3-yl] glyoxylamide or its hydrochloride salt.

12. A method of treating a tumor sensitive to angiogenesis inhibitors, comprising administration to a patient in need of such a treatment of an effective amount of one or more N-substituted indole-3-glyoxylamides compounds selected from the group consisting of:
- N-(pyridin-4-yl)-[1-(4-fluorobenzyl)-indole-3-yl] glyoxylamide,
- N-(pyridin-4-yl)-(1-benzylindole-3-yl)-glyoxylamide,
- N-(4-fluorophenyl)-[1-(3-pyridylmethyl)-indole-3yl] glyoxylamide,
- N-(pyridin-4-yl)-[1-(4-chlorobenzyl)-indole-3-yl] glyoxylamide, and
- N-(pyridin-4-yl)-[1-(4-fluorobenzyl)-indole 3-yl] glyoxylamide HCl, or a physiologically tolerable acid addition salt or a N-oxide thereof.

* * * * *